United States Patent [19]

Johnson

[11] Patent Number: 4,471,865
[45] Date of Patent: Sep. 18, 1984

[54] PACKAGING MACHINES

[75] Inventor: Reginald F. Johnson, Lea, near Gainsborough, England

[73] Assignee: Baker Perkins Holdings PLC, Peterborough, England

[21] Appl. No.: 368,320

[22] Filed: Apr. 14, 1982

[30] Foreign Application Priority Data

May 14, 1981 [GB] United Kingdom ............... 8114733

[51] Int. Cl.³ .......................................... B65G 47/24
[52] U.S. Cl. ................................ 198/408; 198/410; 198/415
[58] Field of Search ............... 198/407, 408, 410, 412, 198/462, 416, 415, 411

[56] References Cited

U.S. PATENT DOCUMENTS

| | | | |
|---|---|---|---|
| 4,020,614 | 5/1977 | Smithers | 198/462 |
| 4,122,938 | 10/1978 | Walz et al. | 198/416 |
| 4,346,800 | 8/1982 | Bennett et al. | 198/412 |

FOREIGN PATENT DOCUMENTS 7705670  5/1977  Netherlands ...................... 198/416

*Primary Examiner*—Joseph E. Valenza
*Assistant Examiner*—Kyle E. Shane
*Attorney, Agent, or Firm*—Watson, Cole, Grindle & Watson

[57] ABSTRACT

Article feeding apparatus includes a series of equally spaced pushers for advancing along a platform a procession of sweets or the like lying flat on the platform. The platform has a downwardly extending ramp and as the sweets travel down the ramp they are turned through 90° to an erect position under control of one or more restraining fingers which move in timed relationship with the pushers. A further turnover device may be provided for turning the erected sweets through a further 90°.

5 Claims, 8 Drawing Figures

PACKAGING MACHINES

BACKGROUND OF THE INVENTION

1. Field of the Invention

This invention concerns an apparatus for collating articles into batches and more particularly to an apparatus for rapidly feeding wrapped articles along a conveyor by pusher members which cooperate with a rotating article restraining device.

2. Description of the Prior Art

It is known to apply wrappers to individual sweets and like articles by a primary wrapper and to feed the wrapped articles along a platform as a uniformly spaced procession by a series of regularly pitched pushers which engage behind and advance the individual articles which lie flat on the platform when delivered onto it from the primary wrapper. The purpose of this is to collate the articles into batches, which are thereafter fed to an overwrapper which applies a further wrapper to each collated batch.

If it should be desired to produce over-wrapped batches in which the articles stand erect instead of flat, it is necessary to turn each article in the procession from the flat to the erect orientation prior to collation and this presents a considerable problem in a modern high speed packaging machine which is required to wrap the articles at a speed as high as 1000 articles per minute.

A first approach to the problem is to provide a ramp in the platform, down which the articles are moved by the pushers from an initial higher level, at which the articles are delivered to the platform from the primary level, to a lower level at which collation is effected. It has been found, however, that this alone is insufficient because at high speeds of operation the articles tend to overshoot the ramp and arrive at the lower level of platform in a flat rather than an erect condition. As will be appreciated, failure of only a single article to be turned through 90° as it moves down the ramp will necessitate stoppage of the machine until the fault is corrected.

SUMMARY OF THE INVENTION

The invention provides article feeding apparatus including a platform having an upper horizontal portion, a lower horizontal portion and an upwardly convex curved ramp leading from the upper to the lower portion, a chain conveyor carrying a series of regularly pitched pushers arranged to feed along the upper portion of the platform and down the ramp a procession of individual sweets or like articles lying flat on said upper portion and restraining device moving in timed relationship with and co-operating with the pushers, which includes a finger arranged to co-operate with the leading end of each article as it reaches the ramp to cause the article to conform with the ramp and turn through 90° to an erect position as it reaches the lower portion of the platform and thereafter to move away from the erected article to free it for continued advance by its pusher.

The restraining device is conveniently constituted by a positively rotated paddle wheel carrying a single blade constituting the finger, which coacts with each article in the procession, or a plurality of equally spaced blades which coact with consecutive articles in the procession.

It is sometimes a requirement that, instead of undergoing overwrapping, batches in which the articles lie flat should be further collated into retangular assemblies for insertion into display cartons. This could be achieved by omission of the ramp and the associated turning of the articles but this would not be acceptable for the following reason.

The articles delivered to the platform have the overlap seam in the wrapper applied by the primary wrapper on their top surfaces and the appearance of these seams through the window of a display carton is regarded as objectionable.

The invention accordingly includes the provision of a further turn-over device for turning the articles through a further 90°, after they have experienced the initial turning through 90° as they pass down the ramp, so that they lie flat in the collated batches with the seams underneath.

BRIEF DESCRIPTION OF THE DRAWINGS

Various other objects, features and attendant advantages of the present invention will be more fully appreciated as the same becomes better understood from the following detailed description when considered in connection with the accompanying drawings, in which like reference characters designate like or corresponding parts through the several views and wherein.

DETAILED DESCRIPTION OF THE PREFERRED EMBODIMENT

Figure 1:
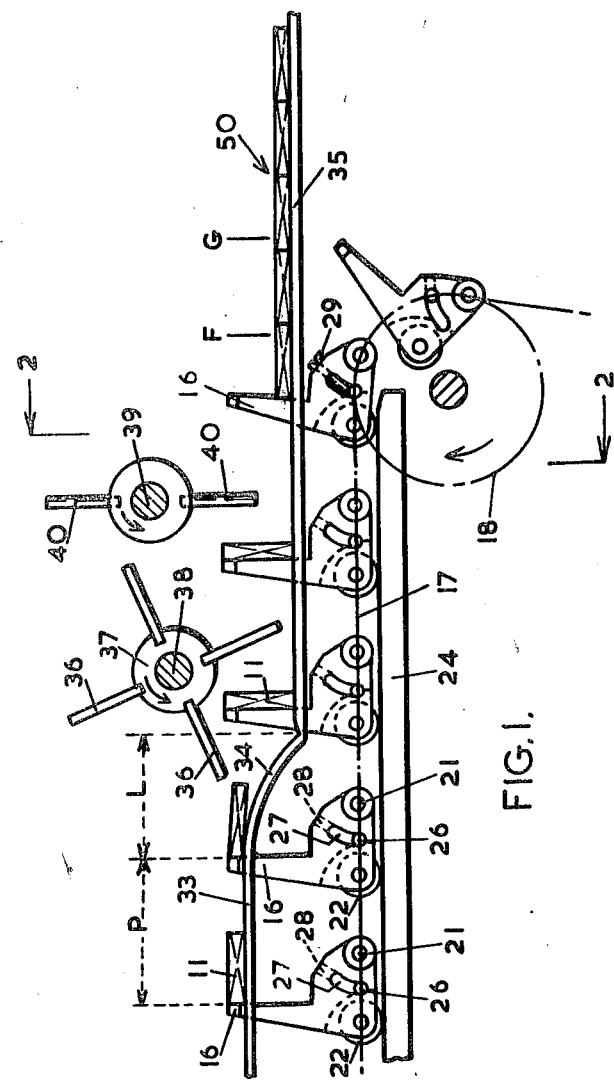
FIG. 1 is a side elevation of the portion of the apparatus which turns sweets, supplied by a primary wrapper, first through 90° and then through a further 90°, prior to batching.

The apparatus illustrated in FIG. 1 includes a platform having an initial horizontal portion 33 which merges, through an upwardly convex curved ramp 34, into a horizontal portion 35 at a lower level than the portion 33.

As described in my co-pending application Ser. No. 368,351, filed Apr. 14, 1982, sweets 11 wrapped in a primary wrapper are delivered from the primary wrapper to the platform and are advanced along the platform as a regularly spaced procession by pusher 16 of a chain conveyor, which extend upwardly through a slot 14 in the platform. The pushers 16 are pivoted at 21 to the chains 17 of the conveyor, which extend around sprockets, one of which is shown at 18.

Each pusher 16 carries a roller 22, which coacts with a cam track 24 and normally maintains the pusher in an upright position. Pegs 26, secured to the chains 17 at intervals, engage arcuate slots 27 in the pushers. The pushers have threaded holes 28 which communicate with the slots 27 and when, as illustrated, batches of five sweets are to be collated, a screw 29 is inserted into the hole 28 in each fifth pusher so that its tip precludes movement of the peg 26 in the slot 27 of that pusher.

Figure 7:
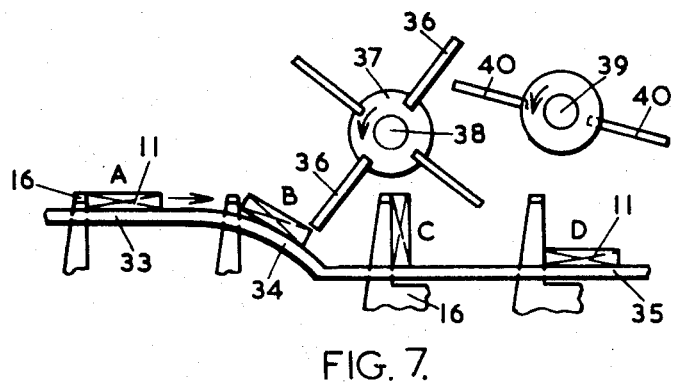
Figure 8:
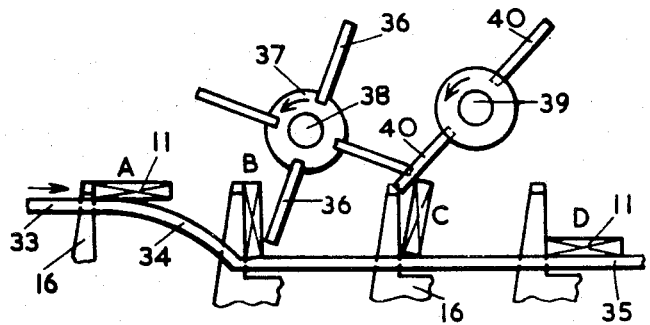

A hub 37, mounted on a shaft 38, carries four radially projecting blades 36. The shaft 38 rotates at a speeed such that it performs a quarter of a revolution for each advance of the chain conveyor through the distance P constituting the pitch of the pushers 16. The blades 36 coact with the pushers 16 as shown in FIGS. 6–8 to ensure that each sweet will be turned through 90° as it descends the ramp 34.

Figure 3:
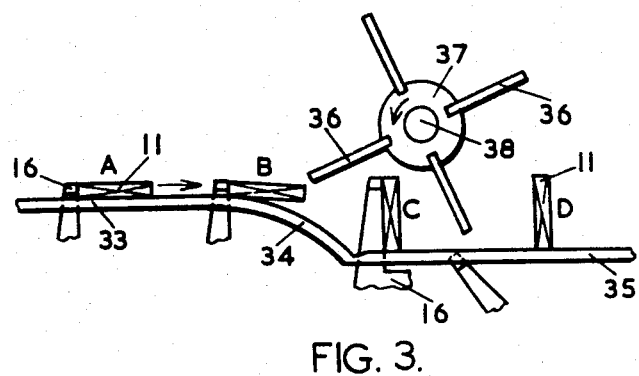
FIGS. 3 to 8 are diagrams illustrating successive stages in the turning operation.
Figure 4:
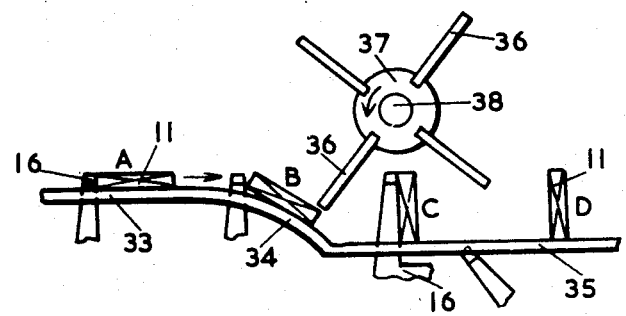
Figure 5:
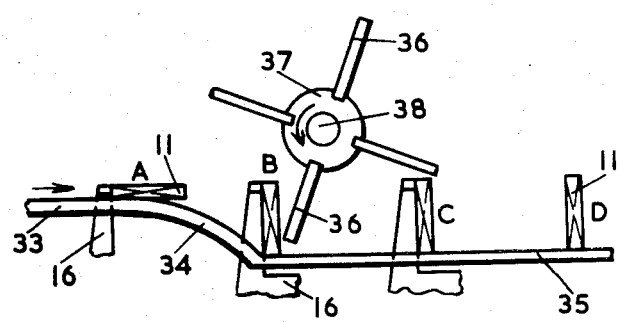

As each sweet reaches the ramp 34 one of the blades 36 engages a leading edge of the sweet to ensure that it does not overshoot the ramp. FIG. 3 shows the sweet B about to leave the platform 33 and pass down the ramp 34, sweets C and D having already passed down the ramp and been turned through 90° on to their edges. At this position one of the blades 36 is about to engage the leading edge of the sweet B. FIG. 4 shows the sweet B approximately half way down the ramp with the blade 36 guiding the leading edge of the sweet in a downward direction towards the portion 35 of the platform. FIG. 5 shows the sweet B turned on to its edge at the base of the ramp and the blade 36 moving away from the sweet. As the sweet B is moved along the portion 35 of the platform by its pusher away from the ramp, the sweet A is being moved by its pusher towards the ramp and the turn-over cycle is repeated, the next succeeding blade 36 ensuring that the sweet A does not overshoot the ramp.

Figure 2:
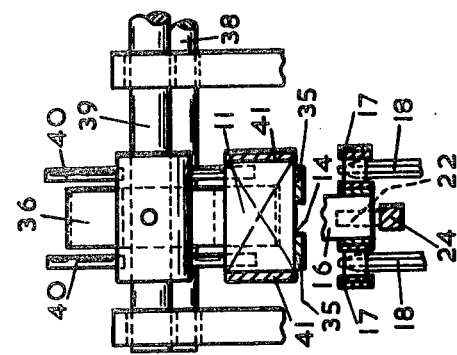
FIG. 2 is a section on the line 2—2 in FIG. 1.

Beyond the shaft 38 is a shaft 39, which rotates at twice the speed of shaft 38 and carries two pairs of diametrically opposed spaced fingers 40 which intermesh with the blades 36 as shown in FIG. 2. These fingers 40 operate to turn the erected sweets 11 through a further 90° as indicated in FIGS. 6-8. During this second turning operation the sweets are supported by side guides 41.

Figure 6:
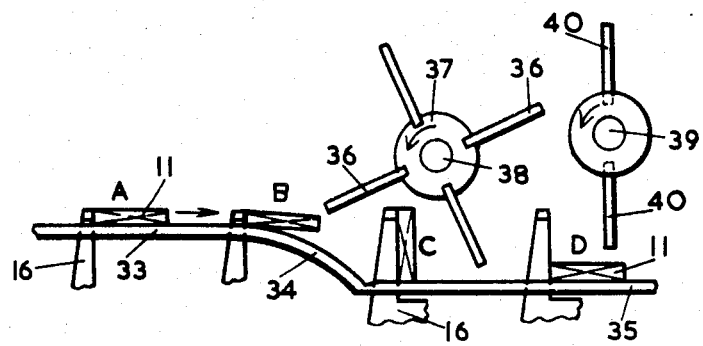

FIG. 6 shows the sweet B about to pass down the ramp 34 under the guidance of the pusher 16 and co-operating blade 36. Sweet C has already passed down the ramp and been turned through 90°, and sweet D has been turned over through a further 90° by one of the pairs of fingers 50. FIG. 7 shows the sweet B approximately half way down the ramp, and sweet C being moved by its pusher along the portion 35 of the platform towards the fingers 40. FIG. 8 shows the sweet B turned through 90° at the base of the ramp 34 and sweet C being engaged by the fingers 40 to turn it through 90° into the flat state.

Each pusher 16 not fitted with a screw 29 tilts rearwardly out of contact with the sweet in advance of it when its roller 22 leaves the end of the cam track 24. Each pusher 16 fitted with a screw 29, however, continues to engage its sweet until it travels around the end sprocket 18, causing that sweet and the four in front of it to form a batch 50 of five sweets. Pushers without screws advance the sweets in front of them to position F while each pusher with a screw advances a collated batch of sweets to position G. Each collated batch is transferred laterally, after its trailing edge has reached position G, from the portion 35 of the platform by a cross pusher (not shown), the batches being subsequently assembled for packing, manually or automatically, in display cartons.

As will be appreciated, each of the blades 36 acts as a restraining finger in conjunction with a pusher 16 to control the movement of a sweet descending the ramp 34.

The paddle wheel formed by the hub 37 and its blades 36 need not necessarily have four blades. If it, for example, had three blades its speed of rotation would need to be such that each blade moves through ⅓ of a revolution for each advance of the chain conveyor through the pitch distance P. Similarly, if the paddle wheel had a single blade only, its speed of rotation would be such that the blade performs a complete revolution for each advance of the chain conveyor through the pitch distance P.

As an alternative to using one or more blades of a rotating paddle wheel to control the sweets as they descend the ramp 34, it is possible to use a restraining finger, the tip of which is moved in an elliptical path in the vertical plane of FIG. 1, rather than in a circular path as in the case of the blades 36, under cam control or through a suitable linkage.

A restraining finger moving in this fashion but serving a different purpose is described in British Patent application No. 2116135. For present purposes such finger coacts with each sweet, generally in the manner shown in FIGS. 3-5, by engaging the leading end of the sweet to prevent it from overshooting the ramp, guides it down the ramp and subsequently withdraws from the sweet when it has assumed the erect position.

In the embodiment shown in FIG. 1, the upper surface of the ramp 34 is a circular arc tangential to the upper surface of the portion 33 of the platform and the length L of the ramp, measured horizontally, is slightly less than the pitch length P.

Obviously, numerous modifications and variations of the present invention are possible in light of the above teachings. It is therefore to be understood that within the scope of the appended claims, the invention may be practiced otherwise than as specifically described herein.

I claim:

1. Article feeding apparatus comprising a platform having an upper horizontal portion, a lower horizontal portion and an upwardly convex curved ramp leading from the upper to the lower portion, a chain conveyor carrying a series of regularly pitched pushers arranged to feed along the upper portion of the platform and down the ramp a procession of individual sweets or like articles lying flat on said upper portion and restraining means moving in timed relationship with and cooperating with the pushers, said restraining means including a restraining finger arranged to travel in front of and cooperate with a leading end of each article as it reaches the ramp to prevent the article overshooting the ramp and cause the article to conform with the ramp and turn through 90° to an erect position as it reaches the lower portion of the platform and thereafter to move away from the erected article to free it for continued advance by one of said pushers.

2. Apparatus according to claim 1, in which the restraining means is a positively rotated paddle wheel carrying at least one blade constituting the finger.

3. Apparatus according to claim 2, in which the paddle wheel carries a plurality of equally spaced blades which coact with consecutive articles in the procession.

4. Apparatus according to claim 1, wherein the length of the ramp, measured horizontally, is slightly less than the pitch distance between the pushers.

5. Apparatus according to claim 1, which includes a further turn-over device located above the lower portion of the platform and operative to turn each erected article through a further 90° as it is advanced by the pushers along said lower portion.

* * * * *